(12) United States Patent
Lohmer et al.

(10) Patent No.: US 10,023,507 B2
(45) Date of Patent: Jul. 17, 2018

(54) DECOMPOSITION OF ETHERS

(71) Applicant: INEOS SOLVENTS GERMANY GMBH, Moers (DE)

(72) Inventors: Gunther Lohmer, Mulheim an der Ruhr (DE); Dirk Schnitzler, Herne (DE); Vanessa Manz, Essen (DE)

(73) Assignee: INEOS SOLVENTS GERMANY GMBH, Moers (DE)

( * ) Notice: Subject to any disclaimer, the term of this patent is extended or adjusted under 35 U.S.C. 154(b) by 0 days.

(21) Appl. No.: 15/807,696

(22) Filed: Nov. 9, 2017

(65) Prior Publication Data

US 2018/0127330 A1     May 10, 2018

(30) Foreign Application Priority Data

Nov. 9, 2016   (EP) .................................... 16197985

(51) Int. Cl.
*C07C 1/22* (2006.01)
*C07C 29/04* (2006.01)

(52) U.S. Cl.
CPC ................ *C07C 1/22* (2013.01); *C07C 29/04* (2013.01); *C07C 2521/04* (2013.01)

(58) Field of Classification Search
CPC .................................. C07C 1/22; C07C 29/04
USPC .......................................................... 568/895
See application file for complete search history.

(56) References Cited

U.S. PATENT DOCUMENTS 4,357,147 A     11/1982 Bezman

FOREIGN PATENT DOCUMENTS

| | | | |
|---|---|---|---|
| JP | H 03123738 A | 5/1991 | |
| JP | 2749664 B2 | 2/1998 | |

*Primary Examiner* — Sikarla A Witherspoon
(74) *Attorney, Agent, or Firm* — Nixon & Vanderhye P.C.

(57) ABSTRACT

A process for producing propylene or butene is disclosed, comprising passing a stream comprising 10-70 wt % of diisopropyl ether or 30-95 wt % of di-sec butyl ether over an acid catalyst at a temperature of 180-300° C. and a pressure of 0.01-3 bar g. Also disclosed is a process for producing either isopropanol or 2-butanol, comprising contacting water and a propylene- or butene-containing feedstock in a hydration reaction zone with a hydration catalyst to produce a stream comprising either isopropanol and a by-product stream or 2-butanol and a by-product stream, passing said by-product stream over an acid catalyst at a temperature of 180-300° C. and a pressure of 0.01-3 bar g to produce either propylene or butene, and then recycling said propylene or butene to the hydration reaction zone.

7 Claims, No Drawings

DECOMPOSITION OF ETHERS

This new application claims priority to European Patent Application No. 116197985.1 filed Nov. 9, 2016, the entire contents of each of which are hereby incorporated by reference.

This invention relates to the selective decomposition of ethers to the corresponding alkenes and alkanols and also to the production of isopropanol from propylene and 2-butanol from butene (butylene).

The conversion of ethers to their corresponding alkenes and alkanols is an important reaction in a number of commercial processes. Thus, for example, this reaction is used to remove ethers, such as isopropyl ether, produced as the by-products of other processes, such as the hydration of propylene to produce isopropanol. Isopropanol may be made with very high propylene conversions using even dilute C3 olefin-containing feedstocks. However under some conditions large amounts of diisopropyl ether (DIPE) may be formed. In addition, an important route for the production of tertiary olefins involves the reaction of mixed olefins with an alcohol over an acid catalyst to selectively produce a tertiary alkyl ether, separation of the ether from the remaining olefin stream, and then decomposition of the ether to the desired tertiary olefin. This latter process relies on the fact that tertiary olefins react with alcohols more rapidly than either secondary or primary olefins. However for this reason, the production of secondary olefins from the decomposition of secondary ethers is less straightforward.

U.S. Pat. No. 4,357,147 discloses a process for producing oxygenated fuel blending compositions, in which water and a propylene-containing feedstock are first reacted with a hydration catalyst to produce isopropanol and diisopropyl ether (DIPE). The DIPE is then separated in a distillation column, and the resulting overhead stream comprising mainly DIPE, as well as about 4% isopropyl alcohol (IPA) and 5% water, is contacted with a reversion catalyst under reversion conditions to produce propylene, IPA and water. The reversion catalyst is an acid catalyst, preferably a silica-alumina cogel or a zeolite. Typical reversion conditions are a temperature in the range 120-290° C., with lower acidity catalysts requiring higher temperatures, and a pressure in the range from atmospheric pressure to 35 barg.

JP 03123738A (JP 2749664B2) discloses a process for producing propylene from diisopropyl ether by reacting it in the vapour phase with a solid acid catalyst at a temperature of 150-500° C. In the Examples, isopropyl ether was contacted with a gamma-alumina catalyst at a temperature of 320° C. or 380° C. and a pressure of 7 barg or 18 barg to give propylene at 99.8% conversion and 99.3% selectivity.

In the above cases, the isopropyl ether feedstock used to produce the propylene is relatively pure, and there is no suggestion that the processes disclosed would be effective with impure feedstocks containing significant amounts of other compounds such as n-propyl ether, isopropanol and higher olefins. However the present inventors have discovered that under particular conditions it is possible to obtain propylene from isopropyl ether at high yield with high selectivity even when using an impure feedstock containing no more than 70% DIPE.

Accordingly, in a first aspect the present invention provides a process for producing propylene or butene, comprising passing a stream over an acid catalyst at a temperature of 180-300° C. and a pressure of 0.01-3 bar g, which stream comprises 10-70 wt % of diisopropyl ether, 2-10 wt % of isopropanol and 20-85 wt % of $C_6$-$C_{12}$ olefins in the case of propylene or 30-95 wt % of di-sec butyl ether, 0-20 wt % of 2-butanol and 10-45 wt % of $C_8$-$C_{12}$ olefins in the case of butene.

A further aspect of the invention provides a process for producing either isopropanol or 2-butanol, comprising contacting water and a propylene- or butene-containing feedstock in a hydration reaction zone with a hydration catalyst to produce either:

a stream comprising isopropanol and a by-product stream comprising 10-70 wt % of diisopropyl ether, 2-10 wt % of isopropanol and 20-85 wt % of $C_6$-$C_{12}$ olefins, or:

a stream comprising 2-butanol and a by-product stream comprising 30-95 wt % of di-sec butyl ether, 0-20 wt % of 2-butanol and 10-45 wt % of $C_8$-$C_{12}$ olefins;

passing said by-product stream over an acid catalyst at a temperature of 180-300° C. and a pressure of 0.01-3 bar g to produce either propylene or butene, and then recycling said propylene or butylene to the hydration reaction zone.

The stream which is passed over the acid catalyst to produce propylene may additionally comprise up to 85 wt % of other hydrocarbons such as methylpentenes or dimethylheptenes. It may also comprise up to 20 wt % of n-propyl-isopropyl ether. The level of diisopropyl ether is preferably between 25 and 50 wt %. The level of isopropanol is preferably between 2 and 10 wt %. The level of $C_6$-$C_{12}$ olefins is preferably between 30 and 50 wt %.

The stream which is passed over the acid catalyst to produce butene may additionally comprise up to 45 wt % of other hydrocarbons such as dimethylhexenes. The level of di-sec-butyl ether is preferably between 50 and 90%. The level of 2-butanol is preferably between 0 and 15 wt %.

All references below to the process for producing propylene refer to both aspects of the invention.

The process for producing propylene preferably operates at a temperature of 220-270° C. The pressure is preferably 0.01-1.8 bar g, more preferably 0.01-1.5 bar g.

The catalyst used for producing propylene or butene may be any acid catalyst, such as an acid ion exchange resin catalyst, a silica-alumina cogel, alumina, aluminosilicate or zeolite. Alumina catalysts are most preferred, particularly a gamma-alumina oxide.

For the step of producing isopropanol from water and a propylene-containing feedstock, any known process may be employed. In propylene hydration, a propylene-containing feedstock is generally mixed with water and the mixture is then fed to a reactor to contact the catalyst.

The product stream from the hydration is then distilled to remove the bulk of the isopropanol and water. The waste stream from this distillation typically contains 25-50 wt % of diisopropyl ether, 2-10 wt % of isopropanol and 30-50 wt % of $C_6$-$C_{12}$ olefins. It may also contain water, propylene, propane, any $C_4$ hydrocarbons present in the feed, and traces of alcohols or ethers derived from reactions of $C_4$ hydrocarbons.

The waste stream is first preheated, and then contacted with a gamma-alumina oxide catalyst at a temperature of 180-300° C. and a pressure of 0.01-3 bar g to produce propylene. The conversion of DIPE to propylene is typically at least 80%, preferably at least 95%. The propylene-containing product stream is cooled and then passed through a phase separator, in which propylene is separated off to be recycled to the hydration reactor.

For the step of producing 2-butanol from water and a butene-containing feedstock, any known process may be employed. In butene hydration, a butene-containing feedstock is generally mixed with water, and the mixture fed to a reactor to contact the catalyst. The product stream from the hydration is then distilled to remove the bulk of the 2-butanol and water. The waste stream from this distillation typically contains 30-95 wt % of di-sec butyl ether, 0-20 wt % of 2-butanol and 10-45 wt % of $C_8$-$C_{12}$ olefins. It may also contain water, butene, butane, any $C_3$ or $C_4$ hydrocarbons present in the feed, and traces of alcohols or ethers derived from reactions of $C_3$ or $C_4$ hydrocarbons.

The waste stream is first preheated, and then contacted with a gamma-alumina oxide catalyst at a temperature of 180-300° C. and a pressure of 0.01-3 bar g to produce butene. The butene-containing product stream is cooled and then passed through a phase separator, in which butene is separated off to be recycled to the hydration reactor.

EXAMPLES 1-3

A feed stream containing 35-40% of diisopropyl ether as well as n-propyl-isopropyl ether was contacted with a gamma alumina oxide catalyst in a fixed bed reactor having a catalyst depth of 150 mm at a temperature of 300° C. The pressure was varied in each Example, and the % conversion to diisopropyl ether and n-propyl-iso-propyl ether was recorded. The results are shown below.

| Example | Pressure (bar a) | Conversion (%) |
|---|---|---|
| 1 | 1.0 | 94.34 |
| 2 | 1.28 | 93.86 |
| 3 | 2.0 | 88.56 |

The above results show that conversion declines at higher pressures, with atmospheric pressure giving the highest conversion.

The invention claimed is:

1. Process for producing propylene or butene, comprising passing a stream over an acid catalyst at a temperature of 180-300° C. and a pressure of 0.01-3 bar g, which stream comprises 10-70 wt % of diisopropyl ether, 2-10 wt % of isopropanol and 20-85 wt % of $C_6$-$C_{12}$ olefins in the case of propylene or 30-95 wt % of di-sec butyl ether, 0-20 wt % of 2-butanol and 10-45 wt % of $C_8$-$C_{12}$ olefins in the case of butene.

2. Process for producing either isopropanol or 2-butanol, comprising contacting water and a propylene- or butene-containing feedstock in a hydration reaction zone with a hydration catalyst to produce either:
   a stream comprising isopropanol and a by-product stream comprising 10-70 wt % of diisopropyl ether, 2-10 wt % of isopropanol and 20-85 wt % of $C_6$-$C_{12}$ olefins, or:
   a stream comprising 2-butanol and a by-product stream comprising 30-95 wt % of di-sec butyl ether, 0-20 wt % of 2-butanol and 10-45 wt % of $C_8$-$C_{12}$ olefins;
   passing said by-product stream over an acid catalyst at a temperature of 180-300° C. and a pressure of 0.01-3 bar g to produce either propylene or butene, and then recycling said propylene or butene to the hydration reaction zone.

3. Process according to claim 1, wherein the acid catalyst for producing propylene or butene is selected from an acid ion exchange resin catalyst, a silica-alumina cogel, alumina, aluminosilicate or a zeolite.

4. Process according to claim 1, wherein the stream is passed over the acid catalyst at a temperature of 220-270° C.

5. Process according to claim 1, wherein the stream is passed over the acid catalyst at a pressure of 0.01-1.8 bar g.

6. Process according to claim 1, wherein the stream passed over the acid catalyst to produce propylene comprises 25-50 wt % of diisopropyl ether and/or 2-10 wt % of isopropanol.

7. Process according to claim 1, wherein the stream passed over the acid catalyst to produce butene comprises 50-90 wt % of di-sec-butyl ether and/or 0-15 wt % of 2-butanol.

* * * * *